United States Patent
Benoit et al.

(10) Patent No.: US 11,037,666 B1
(45) Date of Patent: Jun. 15, 2021

(54) METHOD AND APPARATUS FOR DETECTING DIVERTED DRUGS

(71) Applicant: Bottomline Technologies (de) Inc., Portsmouth, NH (US)

(72) Inventors: Mark Benoit, Seattle, WA (US); Benjamin Smith, Hampden, ME (US); Shawn Curtiss, O'Fallon, MO (US)

(73) Assignee: Bottomline Technologies, Inc., Portsmouth, NH (US)

( * ) Notice: Subject to any disclaimer, the term of this patent is extended or adjusted under 35 U.S.C. 154(b) by 148 days.

(21) Appl. No.: 16/425,512

(22) Filed: May 29, 2019

(51) Int. Cl.
| | | |
|---|---|---|
| *G16H 20/10* | (2018.01) | |
| *H04L 12/26* | (2006.01) | |
| *G06N 20/00* | (2019.01) | |
| *G16H 10/60* | (2018.01) | |

(52) U.S. Cl.
CPC ............ *G16H 20/10* (2018.01); *G06N 20/00* (2019.01); *G16H 10/60* (2018.01); *H04L 43/028* (2013.01); *H04L 43/14* (2013.01)

(58) Field of Classification Search
CPC ........ G16H 20/10; G16H 10/60; G06N 20/00; H04L 43/14; H04L 43/028
See application file for complete search history.

(56) References Cited

U.S. PATENT DOCUMENTS

| | | | |
|---|---|---|---|
| 6,842,736 B1 | 1/2005 | Brzozowski | |
| 9,542,534 B1 | 1/2017 | Ducatt et al. | |
| 2008/0000979 A1* | 1/2008 | Poisner | G06K 19/06046 235/462.01 |
| 2011/0161108 A1 | 6/2011 | Miller et al. | |
| 2014/0149131 A1 | 5/2014 | Bear et al. | |
| 2014/0351924 A1* | 11/2014 | Myers | H04L 63/0435 726/15 |
| 2019/0125986 A1* | 5/2019 | Germinario | A61M 15/0081 |
| 2019/0240430 A1* | 8/2019 | Jackson | A61M 15/008 |
| 2019/0246281 A1* | 8/2019 | Ziskind | H04W 12/0808 |
| 2020/0210774 A1* | 7/2020 | Jakubowicz | G06N 3/0454 |
| 2020/0222627 A1* | 7/2020 | Guerra | A61M 5/16854 |
| 2020/0303047 A1* | 9/2020 | Bostic | G16H 50/20 |

FOREIGN PATENT DOCUMENTS

WO 2017066652 A1 4/2017

OTHER PUBLICATIONS

"Products", Medacist web page, downloaded from https://www.medacist.com/products/ on May 1, 2019.

(Continued)

*Primary Examiner* — Austin J Moreau
(74) *Attorney, Agent, or Firm* — Richard A. Baker, Jr.

(57) ABSTRACT

A method and apparatus for detecting suspicious activities surrounding the management of controlled substances in a medical facility is described herein, where the activities that may indicate the diversion of controlled drugs are flagged for further review. The activities are detected by invigilating application layer network packets, related to controlled substances, on the medical facility network, and processing these packets with a rules engine and machine learning generated rules to make a determination if the circumstances surrounding the packets indicate the diversion of controlled substances.

20 Claims, 2 Drawing Sheets

(56) References Cited

OTHER PUBLICATIONS

"Drug Diversion Digest: Year in Review, $301.1M lost to organizations and payors represents only the tip of the drug diversion iceberg", Protenus, Inc., 2018.
Berge, Keith, et al, "Diversion of Drugs Within Health Care Facilities, a Multiple-Victim Crime: Patterns of Diversion, Scope, Consequences, Detection, and Prevention", Mayo Clinic Proceedings, Jul. 2012; 87(7): 674-682.
"Pyxis ES platform solutions, Help simplify and standardize medication management", Becton, Dickenson marketing brochure, 2016.
Arvin, Marti, "Position Paper: What Can Be Done About Drug Diversion? A Growing Problem for Healthcare Organizations", Cynergistek, Feb. 27, 2018.
Soyka, Edward, et al, "Drug Diversion: A Multidisciplinary Approach", Presentation at the 23rd Annual Compliance Institute in Boston, MA, Health Care Compliance Association, Apr. 7-10, 2019.
Ahlstrom, Janice, "Drug Diversion Prevention & Detection: Using a Comprehensive Risk & Internal Audit Approach", Baker Tilly Vichow Krause LLP, 2018.
Kristof, Tina, "Methods, Trends, and Solutions for Drug Diversion", IAHSS Foundation, IAHSS-F RS-18-01, Feb. 8, 2018.
Wine, Vaughn, "Medicaton Orders and More (Deployed Evening of Jan. 12)", email, Jan. 13, 2017.

\* cited by examiner

METHOD AND APPARATUS FOR DETECTING DIVERTED DRUGS

PRIOR APPLICATIONS

This application is a priority application. However, this document draws material from U.S. Pat. Nos. 9,489,627; 7,831,703; 8,433,791; and 9,529,678, as well as U.S. patent application Ser. No. 16/355,985 each patent and application is incorporated herein by reference.

BACKGROUND

Technical Field

The system, apparatuses and methods described herein generally relate to pharmacological distributions, and more specifically to the detection of drug, medication, and narcotics diversions.

DESCRIPTION OF THE RELATED ART

In the United States in 2010, nearly 4 billion retail prescriptions were filled, with sales totaling $307 billion. The medication most often prescribed, 131.2 million times, was the opioid hydrocodone combined with acetaminophen. The opioid oxycodone combined with acetaminophen was prescribed 31.9 million times. Although most of these sales resulted in the legitimate, targeted administration of pharmaceutical agents to patients, a fraction of the drugs manufactured and prescribed for patients are diverted for illicit purposes. Prescription drug diversion has significant health, legal and social implications. Deaths from misuse of prescription drugs account for a significant proportion of overdose deaths.

In the outpatient setting, there is an elaborate system of checks and balances for prescription, procurement, and dosing of a controlled substance. However, in the health care facility environment, vulnerability to diversion exists when a single provider, out of view of others, is free to engage in drug procurement from central stores, drug preparation, drug administration to patients, and/or disposal of drug waste. Given that controlled substances are often titrated to a desired effect in patients who may have widely varying drug requirements (e.g., as a result of baseline individual variability, acquired habituation, or other factors), in the absence of sufficient controls, it is possible for a single health care worker, without the knowledge or collusion of others, to divert drugs intended for patients.

Recent experience have revealed that such health care workplace drug diversion creates numerous potential victims. Specifically, harm can come not only to drug diverters but also to their patients and co-workers and to the reputation of the health care institution that employs them.

The drugs most commonly involved are analgesics, particularly opioids, and psychoactive drugs, particularly benzodiazepines. The term drugs includes both prescribed medicines as well as illegal drugs and controlled substances. A drug is any substance (other than food that provides nutritional support) that, when inhaled, injected, smoked, consumed, absorbed via a patch on the skin, or dissolved under the tongue causes a physiological (and often psychological) change in the body.

Clearly, drug diversion is a significant problem for health care facilities, one in which solutions are not readily found. There are presently several solutions on the market for logging all drug prescriptions directly from the prescription software and reviewing either manually or automatically through the logs to search for anomalies. Safes or several automated dispensing cabinets ("ADC") are used to store controlled substances. Other solutions place cameras on locations where drugs are transferred from one secure locations to another or from a secure location to a patient. These techniques are typically reactive, discovering the problem long after the diversion has occurred.

However, there are no real time mechanisms currently available to detect drug diversion as the diversion is occurring. This results in diversion evidence disappearing. In addition, when the diversion involves substituting medications intended for a patient, the diversion could prevent patients from receiving their prescribed medications. A real time drug diversion mechanism is needed in the health care industry.

BRIEF SUMMARY OF THE INVENTION

A method for detecting the diversion of controlled substances is described herein. The method is made up of the steps of (1) invigilating application layer network packets on a network; and (2) reviewing said application layer network packets for material related to the controlled substances. If the application layer network packets are related to the controlled substances, (3) executing a rules engine on the contents of the application layer network packets to determine if the application layer network packets contains evidence of a possible controlled substance diversion. If the application layer network packet contains evidence of the possible controlled substance diversion, (4) sending the evidence of the possible controlled substance diversion for further review.

In some embodiments, the method also includes storing the contents of the application layer network packet in a database. The method could also include executing rules created by a machine-learning algorithm on the application layer network packet to determine if the application layer network packets contains evidence of the possible controlled substance diversion. The machine-learning algorithm could utilize a distributed algorithm operating on features located on different devices. The method could also include a step for generating the machine learning rules using a machine learning data set.

The rules engine could compare a patient's toxicology data with the controlled substances dispensed to the patient. It could also compare a patient's biological data with the expected impact of the controlled substance on the patient. Or compare the controlled substance that is dispensed to a patient to a prescription for the controlled substance for the patient. The rules engine could also compare a picture of the controlled substance as it is being dispensed to a picture of the controlled substance listed in the prescription. The rules engine could also compare a location of a patient with a location where the controlled substance is dispensed for said patient.

An apparatus for monitoring network packets on a network is also described here. The apparatus is made up of a network interface device, the network interface device configured to invigilate all traffic on the network, where the network interface device filters out all network traffic except application layer packets. The apparatus also includes a database for storage of information from the application layer packets, and a processor unit connected to the database and the network interface device. The processor unit executes an algorithm to parse the application layer packet and filter out packets that relate to controlled substances, sending the application layer packets related to controlled substances to a rules engine and a machine learning rules set. If the rules engine or the machine learning rules set determine that the application layer packet relates to controlled substances, then the application layer packet related to controlled substances is sent for further review.

In some embodiments, the network interface device is a network switch and in other embodiments it is integrated into a server with the processor unit. The apparatus could include a plurality of network interface devices that monitor a plurality of networks.

An apparatus for monitoring network packets on a network is described here. The apparatus comprises a network interface means, the network interface means configured to invigilate all traffic on the network, where the network interface filters out all network traffic except application layer packets. The apparatus also includes a database for storage of information from the application layer packets and a processor unit connected to the database and the network interface. The processor unit executes an algorithm to parse the application layer packet and filter out packets that relate to controlled substances, sending the application layer packets related to controlled substances to a rules engine means and a machine learning rules means. If the rules engine means or the machine learning rules means determine that the application layer packet relate to controlled substances, the application layer packet related to controlled substances is sent for further review.

DETAILED DESCRIPTION

Figure 1:
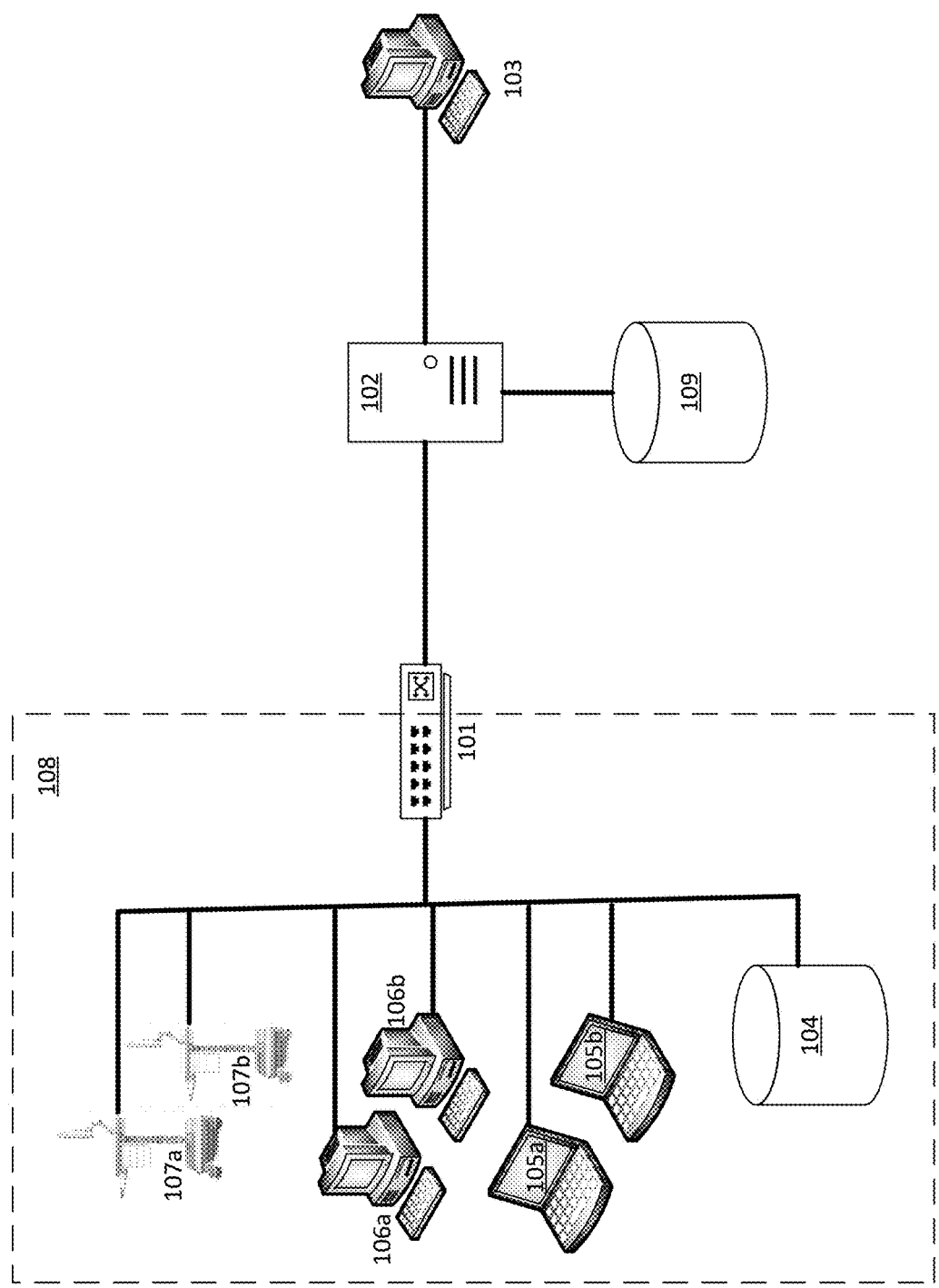
FIG. 1 is an electrical network diagram of the various components of the medical network with the apparatus for detecting drug diversion.

In order to detect medical facility drug diversion in real time, an architecture is outlined in FIG. 1 that shows a system for monitoring activities on the network in the hospital. The hospital network 108 could contain an application database (or database server) 104, various laptops 105a, 105b, personal computers 106a, 106b, automated dispensing cabinets (ADCs) 107a, 107b and other devices as well as a network switch 101. The database 104 could include the pharmacy management software (such as Omnicel), the hospital billing software, the timecard software (Kronos or similar), human resources software (Peoplesoft, ADP), the patient record software (Epic, et al), and any other software and data repositories necessary to operate a hospital or other medical facility. The laptops 105a, 105b, personal computers 106a, 106b or similar devices access these software applications. In addition, special hospital equipment, such as ADCs 107a, 107b, secure drug dispensing carts, also access the database 104 through the network 108.

In a typical drug-dispensing scenario, a doctor will issue a prescription on a laptop 105a, 105b, personal computers 106a, 106b, or similar device (cell phone, tablet, smart watch, etc). The script is sent over the network to the database 104. The switch 101 will see the script and send a copy of it on to the server 102. The pharmacist sees the script, and fills the script, in some embodiments, by placing the medicine in a secure ADC 107a, 107b This transaction is seen on the network 108, and is retransmitted by the switch 101 to the server 102. (In some embodiments, commonly used drugs are stored on the ADC 107a, 107b in quantity and dispensed by nurses on the floor when the ADC sees the prescription. A nurse will then take the ADC 107a, 107b to the patient's room, and remove the medicine for the patient. Since the ADC is secure and locked, the opening of the ADC 107a, 107b by the nurse may require that the nurse log into the ADC with a password, biometrics, or an ID card (bar code or RFID). Removing the medication also sends a message over the network to the database 104 in a transaction that is seen and retransmitted by the switch 101.

On the network 108, a switch 101 is used to route messages within the network 108. The switch 101, in this embodiment, operates in a promiscuous user mode, invigilating (listening to or monitoring but not interfering with) all packets on the hospital network 108, and sending all messages to an off-network location for storage and processing (the server 102 in FIG. 1). In some embodiments, this switch 101 uses the CALEA (Communications Assistance for Law Enforcement Act, a US Law that allows all network traffic to be wiretapped) wiretap port (this is also called SPAN port or mirror port). In other embodiments, a product similar to the NetScout switch family, provides network switching and an understanding of the packets is used. In some embodiments, the switch collects all packets, and analyses the packets within the switch 101, filtering out unwanted traffic such as various packets to create connection and routing information. In another embodiment, the sniffer 101 is a network device dedicated to collecting all network traffic and analyzing it, similar to the Gigamon Insight or TAP products. The switch 101 may report only application level messages and perhaps only messages from a limited subset of devices. For instance, the hospital network 108 could include messages for accounting and VoIP messages that are not of interest. In this embodiment, messages for devices that are not of interest are excluded at the switch level. Depending on the capabilities of the switch 101 a significant amount of network traffic could be filtered to allow the server 102 to focus only on what is necessary. In some embodiments, only traffic related to the pharmacy application is captured by the switch 101 and sent to the server 102.

In some embodiments, the switch 101 is replaced with a network interface chip on a server 102 that operates in promiscuous user mode. In this case, the server 102 receives all of the raw network traffic. In still another embodiment, a separate computer with a network interface chip that operates in promiscuous user mode replaces the switch 101 functionality to capture and filter the packets on the network 108. In still another embodiment, the network interface functionality 101 is integrated into the server processor unit 102.

The server 102 in some embodiments is a set of one of more processors in a processing unit. The server 102 could incorporate internal memory and storage 102. In other embodiments, the storage is separate 109. The server 102 could be a laptop, personal computer, a server, or a complete server farm. The server 102 could be integrated in the investigator personal computer 103.

The system includes at least one sniffer 101 that invigilates network traffic (i.e., packets) conveyed by the entities in the network 108. The sniffer 101 can connect to the network by any applicable mean, such as connecting to a mirror port of a network switch 101 as illustrated in FIG. 1. It should be appreciated that each sniffer 101 can be pre-configured to invigilate network packets conveyed by or to one certain server 102. In a different embodiment at least some of the sniffers 101 can be pre-configured to invigilate packets conveyed by or to more than one host.

Connecting the at least one sniffer 101 to a mirror port is non-limiting and alternative methods are also applicable, such as using network TAP devices.

The at least one sniffer 101 invigilates host system packets carried by TCP/IP packets and System Network Architecture (SNA) packets that are conveyed by the terminals 105a, 105b, 106a, 106b, 107a, 107b and hosts 104. Generally, the packets invigilated by the sniffers are referred to as "invigilated packets".

The hospital network 108 could be a single segment network or could include a plurality of segments. The hospital network 108 could be a wired or wireless network, or any combination thereof. The hospital network 108 could include a virtual private network (VPN). Multiple switches 101 may be required, depending on network architecture, to see the network traffic of interest, each transmitting the packets of interest to the server 102. While we use the term hospital network, the present invention applies to networks in other facilities, include nursing homes, doctor's offices, pharmacies, veterinary hospitals, retirement/assisted living, Skilled Nursing Facilities, mental health facilities, surgery centers, etc.

The switch 101 transmits all of the traffic of interest seen on the hospital network 108 to the server 102. The server may record all of the traffic in a database 109 (creating a message log) and may process the network packets in real time as they are received. The database 109 may also include other information relevant to drug diversion detection, such as a database of patients, patient medical records, a list of all prescriptions and drugs dispensed, and/or a database of employee information (including timecards). The database 109 could also include drug information, a list of controlled substances, and could be used to store processed information gleaned from the network traffic.

One or more investigator computers 103 (could be laptops, iPads, smart watches, smart phones, or similar devices) are connected, directly or through a network, to the server 102 to allow a drug diversion investigator to review alerts and information related to the distribution of controlled substances in the hospital.

Figure 2:
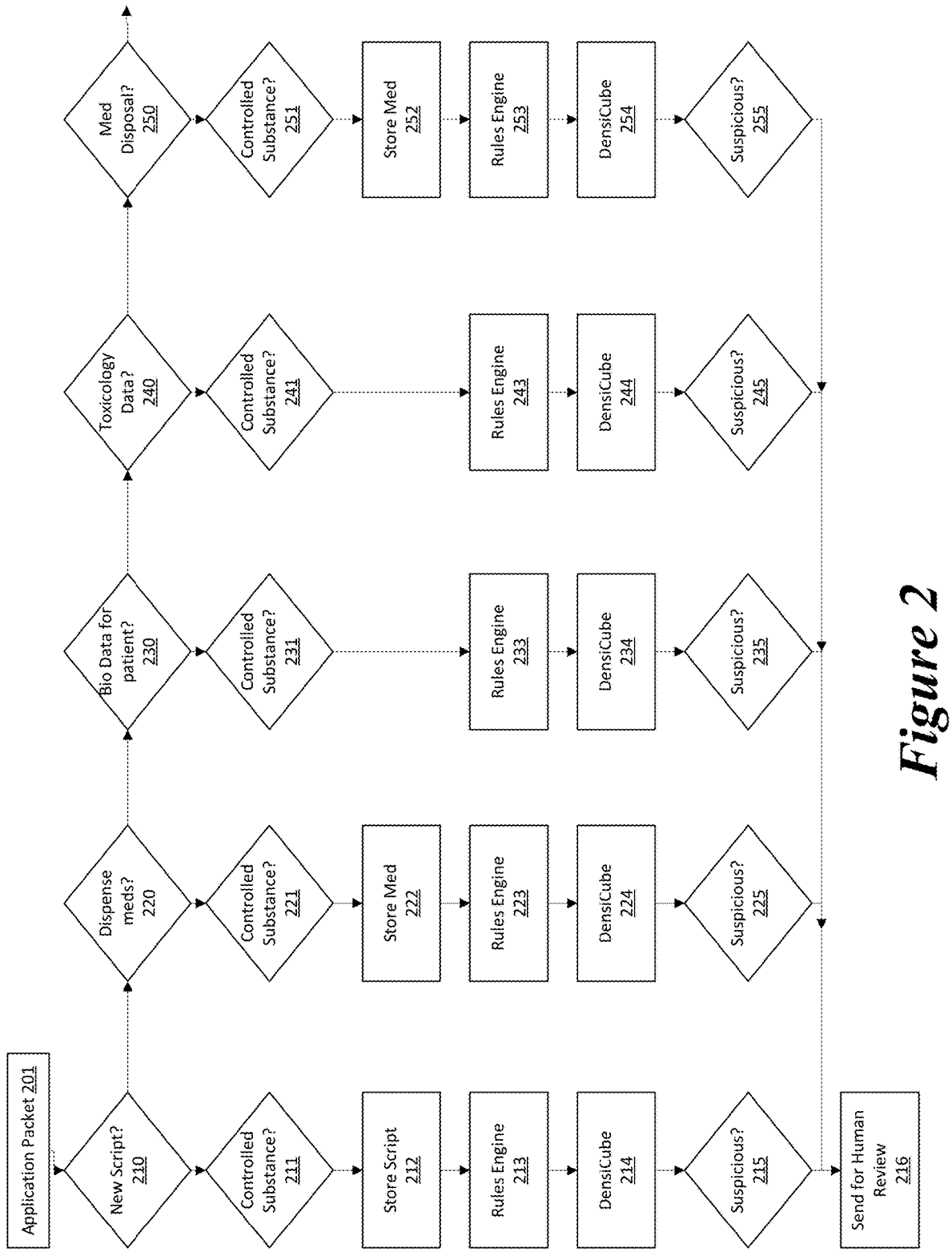
FIG. 2 shows a software architecture for filtering each packet and determining if the packet contains evidence of suspicious activity.

Once the network traffic has been filtered, either by the sniffer/switch 101 or by the server 102, the software within the server 102 takes the application level packet 201 and processes the packet 201 through a combination of machine learning algorithms and/or rules engines. One possible algorithm is outlined in FIG. 2. The application layer packet 201 is first checked to see if the packet contains a new prescription 210. The packet 201 is checked by reviewing the contents of the packet 201, parsing to find the fields related to a prescription (searching for patient name, date, medicine name, dosage, and doctor name). If these fields are found, and an indication that the packet 201 is a prescription, then the algorithm proceeds to check the contents of the prescription 211. In alternative embodiment, the packets are taken from software logs built by the applications (pharmacy management software, the hospital billing software, the timecard software, the patient record software, etc) that manage the databases 104.

If the packet 201 is a new prescription, the software then checks to see if the prescription is for a controlled substance 211. This check is performed by looking up the medicine name in the prescription in a database of controlled substances. This controlled substances database could be located in the database 109. If the prescription is not for a controlled substance, then the prescription is not reviewed further. However, in some embodiments, other medications could be included with the controlled substances for further review, for instance a high priced chemotherapy drug could be reviewed based on the cost.

Next, the details of the prescription, the patient name, date, medicine name, dosage, and doctor name, are stored in the prescription database 212. The prescription database could also be located in the monitoring database 109. The prescription database is used by the rules engines and the machine learning algorithms to determine if other actions are suspicious later in the algorithms in FIG. 2.

The rules engine 213 then checks the data in the script against various data in the database 109. These rules could include (this list is not exhaustive):

a check on the data on the prescription to make sure that the date is the current day to eliminate duplicate prescriptions and prescriptions that are no longer needed. If the prescription is not current, it is flagged for human review 216, but the processing of the prescription continues to find additional anomalies.

comparing the doctor's name on the prescription to a database of doctors with authority to issue prescriptions. This comparison could also include a comparison of the doctor's specialty with the type of medication prescribed, flagging an allergy doctor's prescription for morphine for further review 216, for instance. A comparison of the doctor's specialty to the patient could also be done, making sure a pediatrician is not prescribing opioids to an adult patient. In addition, the sum of the quantity of medication prescribed by the doctor over the past day, week, month, and year could be compared to expected standards for doctors with a similar specialty.

comparing the dosage of prescription to patient data and typical qualities for that particular drug formulation, making sure that the dosage for a 250 pound man is not prescribed to a child. This comparison could also include the overall quantity of this prescription summed with other prescriptions for the patient in the recent past as related to this particular medication and to other similar medications.

the identity of the patient could be compared to the doctors name to be sure that the doctor is not prescribing the controlled substance to himself, the patients name could be compared to the employee database so that a human reviews 216 all internal prescriptions, and the patient's name could be compared to a list of known drug abusers (this could be an internal list or a regional or national "prescription doctor shopping" database that is automatically searched). In addition, the prescription could be compared to a list of current patients in the facility, to assure that prescriptions were not written to discharged patients or patients who have yet to be seen by the doctor. In this set of comparisons, natural language processing techniques could be utilized to match identities that are close but not exact. See U.S. Pat. No. 10,235,356 for further discussion of authentication techniques for non-exactly matching texts, said patent incorporated herein by reference.

finally, the rules engine 213 could check to see if the medicines prescribed are appropriate for the diagnosis in the patient's chart, to check if a patient is receiving oxycodone for the flu, for instance. Throughout all of the rules engine 213 checks, any anomalies are noted and recorded, but the entire set of rules are checked, as is the machine learning rules 214 (possibly using DenisCube machine learning algorithms), before sending the prescription for human review 216. This is to assure that the human review 216 has notice of all of the suspicious attributes of the prescription.

Once the rules engine 213 completes its processing, the machine learning algorithms 214 process additional analysis of the circumstances surrounding the prescription. Separate from algorithms in FIG. 2, a learning data set of features related to prescriptions along with the determination of whether the prescription was involved in drug diversion is run through a machine learning engine, such as the ones for DensiCube described in U.S. Pat. No. 9,489,627 and U.S. patent application Ser. No. 16/355,985 (both incorporated herein by reference). The machine learning engine derives a set of machine learning rules 214 to use in the determination of whether a prescription is suspicious. The prescription found in the application packet 201 is run through the machine learning rules 214 and a confidence score is calculated regarding the suspiciousness of the prescription. If the prescription is thought to be suspicious, it is flagged for human review 216. In some embodiments, the results of the human review 216 are fed back into the machine learning algorithm, either immediately adjusting the algorithm or by including the features of the prescription and the determination into the training dataset for use the next time the machine learning algorithm is calibrated. The features could be any aspect of the prescription, the doctor's employee record, the patient's record, the medication's record, etc that could be used by the machine to find a correlation. For instance, the machine may determine, as one of its rules, that controlled substances prescribed in injectable form to a room near the hospital stairs on Friday afternoons are more likely to be diverted.

If the rules engine 213 or the machine learning rules 214 determine that the prescription is suspicious 215, perhaps by checking a flag set by the rules engine 213 or the machine learning rules 214, then the prescription is reviewed by a human investigator 216. If the checked flag is not set, then the prescription is not checked further.

The human review 216 step involves a human reviewing the prescription and the reasons that the machine believes that the transaction is suspicious. The investigator could indicate that this is a false positive, and the information fed back into the machine learning training set. Or the investigator could agree that the prescription requires additional investigation, and proceed to interview the patient, the doctor or others to determine if disciplinary action needs to be taken. In some cases, the prescription could be canceled. Since the analysis of the packet is performed in real time (or near real time), the investigator is alerted within seconds of the prescription being filed. This provides sufficient time to block the filling of the prescription or to place special precautions on the use of the medications. Alternatively, surveillance could be setup to assure that the prescription is filled and used as intended.

Returning to the question of whether the application packet 201 contains a new prescription 210, if the packet 201 is not a new prescription 210, then the packet is examined to see if it relates to the dispensing of medication 220. This check on the packet 201 could be triggered by a nurse opening a secure drawer on an ADC 107a, 107b, or by a pharmacist opening a secure location to fill the prescription.

If the packet 201 is an indication that medicine is being dispensed, the software then checks to see if the medicine is for a controlled substance 221. This check is performed by looking up the medicine name in a database of controlled substances. This controlled substances database could be located in the database 109. If the medicine is not a controlled substance, then the dispensing transaction is not reviewed further. However, in some embodiments, other medications, such as high cost medicines, could also be sent for further review.

Next, the details of the dispensing order, the date and time, the nurses name, the location of the ADC 107a, 107b cart, the medicine being dispensed, the drawer in the ADC 107a, 107b cart, and the prescription identification used to authorize the opening of the ADC 107a, 107b (including the patient name, date, medicine name, dosage, and doctor name) are stored in the prescription database 222. The prescription database could also be located in the database 109. This data is used by the rules engines and the machine learning algorithms to determine if other actions are suspicious later in the algorithms in FIG. 2.

The information from the packet are next run through the rules engine 223. These rules could include (this list is not exhaustive):

the medicine dispensed is checked against the medicine listed in the prescription. In some embodiments, a photo or video is taken of the medicine being removed from the ADC 107a, 107b and the image is analyzed with software to identify the medicine that is removed from the drawer. This is compared to the prescription to see if there is a match. In some embodiments, the image analysis uses a fuzzy logic algorithm to see if the medicine in the image is plausibly a match with the prescription. If a prescription cannot be found, the circumstances surrounding the dispensing of the medicine are flagged as suspicious.

the date of the prescription is checked to see if the prescription was written within a predetermined time period. Older prescriptions are flagged for further review.

the location of the ADC 107a, 107b when the medicine is dispensed is checked to see if it is located near the location of the patient, based upon the patient's medical record.

the nurse's name is compared to a database of nurses with authority to dispense that that type of medicine. A comparison of the nurse's specialty to the patient could also be done, making sure a pediatric nurse is not prescribing opioids to an adult patient, or to a child with an adult dose. In addition, the sum of the quantity of medication prescribed by the nurse over the past day, week, month, and year could be compared to expected standards for nurse with a similar job classification.

if the medicine is dispensed from the "Crash Cart" in an emergency room, the dispensing without a prescription does not get flagged a suspicious, but additional rules are checked to see if the nurse or doctor pull an unusual number of drugs from the Crash Cart compared to a standard or that the patient's condition warrant the dispensing of the medicines.

in some circumstances, many of the rules checked above for the new prescription rules engine 213 could be run again here.

Once the rules engine 223 completes its processing, the machine learning algorithms 224 process additional analysis of the circumstances surrounding the dispensing of the medicine. Separate from algorithms in FIG. 2, a learning data set of features related to circumstances of the dispensing of the medicine along with the determination of whether the dispensing was involved in drug diversion is run through a machine learning engine, such as the ones for DensiCube described in U.S. Pat. No. 9,489,627 and U.S. patent application Ser. No. 16/355,985 (both incorporated herein by reference). The machine learning engine derives a set of machine learning rules 224 to use in the determination of whether the dispensing is suspicious. The circumstances found in the application packet 201 are run through the machine learning rules 224 and a confidence score is calculated regarding the suspiciousness of the dispensing of the medicine. The machine learning engine could search for relationships between nurses and patients with elevated pain scores, or patients getting certain medications, or navigating to get assigned to certain patients. If the dispensing seems to be suspicious, it is flagged for human review 216. In some embodiments, the results of the human review 216 are fed back into the machine learning algorithm, either immediately adjusting the algorithm or by including the features of the dispensing and the determination into the training dataset for use the next time the machine learning algorithm is calibrated. The features could be any aspect of the dispensing (including the schedule), the nurse's employee and attendance records, the patient's record, the medication's record, patient complaints and satisfaction scores, the location record of the cart, etc. that could be used by the machine to find a correlation. For instance, the machine may determine, as one of its rules, that a drug diversion is likely to occur if the ADC 107*a*, 107*b* cart stops in the cafeteria before heading to the patient's room.

If the rules engine 223 or the machine learning rules 224 determine that the prescription is suspicious 225, perhaps by checking a flag set by the rules engine 223 or the machine learning rules 224, then the circumstances surrounding the dispensing of the medicine is reviewed by a human investigator 216. If the checked flag is not set, then the circumstances are not checked further.

Returning to the question of the subject of the application packet 201, if the application packet 201 relates to biological data related to a patient 230, the data is investigated further for information relevant to the administration of a controlled substance. This biological data could include respiration, heart rate, blood oxygen level, pain level, blood pressure, and similar metrics. The biological data could be reported directly from a monitoring machine or could be reported and entered by a nurse.

If the packet 201 contains biological data 230, the patient identification in the application packet 201 is used to look in the prescription database 109 to see if the patient has recently received a controlled substance 231. If not, the information in the packet 201 is not processed further (in some embodiments, the data is stored in the database 109).

If the patient has recently been given a controlled substance 231, then the biological data is compared, in the rules engine 233) to other stored biological data for the patient (perhaps in database 109 or from the patient's medical records stored in the database 104, or stored elsewhere). If the patient has been given an opioid or other type of pain medication, one or more of the respiration, heart rate, blood oxygen level, pain level, or blood pressure should have gone down as the patient relaxes from the medication. If the patient does not respond after the medicine was given, then there is a suspicion that the drugs intended for the patient were not given to the patient. Thus the situation is flagged as suspicious.

Some level of machine learning algorithms 234 may also be run against the biological data to see if additional insight can be found in the data. This machine learning may incorporate additional aspects of the patient's overall drug regimen and may look at normal biological data ranges for the patient and the time of day (was the patient sleeping, was the patient still under the effect of a previous dose of a pain killer).

If the machine learning 234 or the rules engine 233 notice a suspicious response 235 to the administration of a controlled substance, the circumstances are sent for human review 216. Because the data is received in real time, a toxicological screen could be done on the patient to definitively determine if the prescribed and dispensed dose of the controlled substance was administered to the patient.

Returning to the question of the subject of the application packet 201, if the application packet 201 contains a toxicology report 240, the report is investigated to determine if the patient has been prescribed a controlled substance 241. In most cases, the toxicology report is an ASCII text document that is easily parsed into a drug and value structure, but in other cases it may be a bitmapped or faxed document that requires optical character recognition before analysis. The toxicology report may contain a list of substances found in blood, saliva or urine. If the patient has indications of a controlled substance in the toxicology report or if the patient has been prescribed a controlled substance 241, the processing continues with the rules engine 243. If not, no further analysis is done on the toxicology report.

The rules engine 243 creates a list of the controlled substances in the toxicology report, and checks that a matching prescription and a record that the drug was dispensed to the patient (as found in the database 109). Any mismatches are flagged as suspicious. If the toxicology report quantifies the controlled substances, the amount of each controlled substance in the toxicology report is checked to see if it is within a reasonable range given the time and quantity of the drug that was dispensed to the patient.

A search of the prescription database 109 is also conducted to see if any drugs prescribed and/or dispensed to the patient are missing from the toxicology report. If so, a check is made to see if the prescriptions have been cancelled or to see if the dispensed medicine has been properly disposed of. If there are any prescriptions and/or dispensed medicines that are missing from the toxicology report, those prescriptions and/or dispensed medicines are marked as suspicious.

The machine learning algorithms 244 may also be run against the toxicology to see if additional insight can be found from the features in the toxicology report. This machine learning may incorporate additional aspects of the patient's overall drug regimen and may look at normal biological data ranges for the patient and the time of day (was the patient sleeping, was the patient still under the effect of a previous dose, etc.).

If the machine learning 244 or the rules engine 243 notice a suspicious response 245 to the administration of a controlled substance, the circumstances are sent for human review 216.

Looking once again at the type of application packet 201, if the packet related to the disposal of drugs 250 then the packet and the related information is examined to assure that the drugs are properly disposed. Drug disposal is an area that has been identified as area in which drugs are often diverted. Hospitals and other facilities often have policies (and the US Government has regulations) in place to cover the disposal of drugs to make sure that the medicines are not diverted in the process. Some of these policies/regulations require a witness to verify every drug disposal, and that the drugs are rendered unusable in the disposal process. The present algorithm performs various audits to make sure the drugs are not diverted. In the present case, a nurse or pharmacist records the disposal of the drug in the pharmacy database or in a patient's medical record. Either action is noted in the review of the application packet 201.

Once the packet 201 is identified as a medicine disposal packet 250, the type of drug being disposed is checked against the controller substance list 251. The focus is on controlled substances, but other drugs could be reviewed as well to assure that medicines were not being stolen through the drug disposal process. One could image diverting drugs from the hospital pharmacy to the black market for profit by "disposing" of the drugs. In these cases, the list of controlled substances could be expanded to cover these medicines. If the drug being disposed of is not on the controlled substances list, no further processing is undertaken here.

Once the drug has been confirmed to be a controlled substance, a record of what has been disposed is saved in the database 109 for future reference 252. Note that we use the word disposed and destroyed interchangeably. In some cases, the disposal is a collection of unused drugs that are later destroyed. In other cases, the drugs are destroyed immediately. If the drugs are collected for later destruction, there may be two disposal events for each drug, once when collected and again when physically destroyed.

Then the packet is analyzed by the rules engine 253. The rules engine checks the data regarding the drug being disposed to see if the quantity of the drug being disposed added to the quantity dispensed to the patient is equal to the quantity in the prescription. If the sum is less that the prescription quantity, the transaction is marked as suspicious, indicating that an investigated is warranted to determine where the missing quantity has gone. If the sum is greater than the prescription quantity, the transactions marked as suspicious as the record keeping has been sloppy, which may indicate the opportunity for diversion.

A second rule for the rules engine 253 may look to determine where the drugs are being destroyed. If the medicine is being removed from an ADC cart 107a, 107b, the location within the hospital is checked to see if there are disposal facilities in the room where the disposal is happening. Information about the location may be gleaned from the network location where the packet 201 originated. An Ethernet trace route inquiry could be issued to the IP address where the packet 201 originated. In either case, the location is checked to see if it is in an employee locker room (suspicious) or a pharmacy disposal location (not suspicious).

Another rule that could be checked is to see if a chemical medication disposal device (such as RxDestroyer product) is present in the disposal location, and that the medical disposal device is not full.

The nurse and witness of the disposal could be checked to assure that they are both authorized to handle controlled substances and that they are authorized to dispose of medications.

The machine learning rules 254 generated by the machine learning algorithm (such as DensiCube) could search for more complex situation such as the number of disposals for any particular nurse or witness compared to other nurses and witnesses. Patterns of witness/nurse pairs are investigated to see if particular employees are colluding on drug diversions. The timing of disposals could also be reviewed by the machine learning algorithms to see if there is a relationship between the disposals and the end of shifts or lunch breaks. In addition, the number of disposals per patient may be investigated to see if certain patients, or patient room locations have an unusual number of disposals. Patterns of types of drugs destroyed by certain nurses are investigated. Other features of the disposal circumstances could also be analyzed by the machine learning algorithm.

If the machine learning 254 or the rules engine 253 notice suspicious circumstances 255 to the disposal of a controlled substance, the circumstances are sent for human review 216.

Other types of packets could also be analyzed for information on drug diversion. Any combination of the above descriptions could be performed in the server 102 without deviating from the spirt of the inventions herein.

The foregoing devices and operations, including their implementation, will be familiar to, and understood by, those having ordinary skill in the art. While this disclosure describes the monitoring of the dispensing of drugs, the same techniques could be used to monitor and detect anomalies with medical billing.

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

The invention claimed is:

1. A method of detecting diversion of controlled substances, the method comprising:
    promiscuously invigilating application layer network packets on a network, filtering out all network traffic except application layer network packets;
    reviewing said application layer network packets for material related to the controlled substances;
    if the application layer network packets are related to the controlled substances;
        executing a rules engine on contents of the application layer network packets to determine if the application layer network packets contains evidence of a possible controlled substance diversion;
        if the application layer network packets contains the evidence of the possible controlled substance diversion;
            sending the evidence of the possible controlled substance diversion for further review.

2. The method of claim 1 further comprising storing the contents of the application layer network packets in a database.

3. The method of claim 1 further comprising executing rules created by a machine learning algorithm on the application layer network packets to determine if the application layer network packets contains the evidence of the possible controlled substance diversion.

4. The method of claim 3 wherein the machine-learning algorithm utilizes a distributed algorithm operating on features located on different devices.

5. The method of claim 3 further comprising generating rules for the rules engine using a machine learning data set.

6. The method of claim 1 wherein the rules engine compares a patient's toxicology data with the controlled substances dispensed to the patient.

7. The method of claim 1 wherein the rules engine compares a patient's biological data with an expected impact of the controlled substances on the patient.

8. The method of claim 1 wherein the rules engine compares the controlled substances that are dispensed to a patient to a prescription for the controlled substances for the patient.

9. The method of claim 8 wherein the rules engine compares a picture of the controlled substance as the controlled substance is being dispensed to a picture of the controlled substance listed in the prescription.

10. The method of claim 1 wherein the rules engine compares a location of a patient with a location where the controlled substance is dispensed for said patient.

11. An apparatus for monitoring network packets on a network, the apparatus comprising:
  a network interface device, said network interface device configured to promiscuously invigilate all traffic on the network, where the network interface device filters out all network traffic except application layer packets;
  a database for storage of information from the application layer packets;
  a processor unit connected to the database and the network interface device;
  wherein the processor unit executes an algorithm to parse the application layer packets and filter out packets that relate to controlled substances, sending the application layer packets related to the controlled substances to a rules engine and a machine learning rules set;
  wherein if the rules engine or the machine learning rules set determine that the application layer packet relate to the controlled substances, the application layer packet related to the controlled substances is sent for further review.

12. The apparatus of claim 11 wherein the network interface device is a network switch.

13. The apparatus of claim 11 wherein the network interface device is integrated into a server with the processor unit.

14. The apparatus of claim 11 further comprising a plurality of network interface devices that monitor a plurality of networks.

15. The apparatus of claim 11 wherein the rules engine compares a patient's toxicology data with the controlled substances dispensed to the patient.

16. The apparatus of claim 11 wherein the rules engine compares a patient's biological data with an expected impact of the controlled substances on the patient.

17. The apparatus of claim 11 wherein the rules engine compares the controlled substances that are dispensed to a patient to a prescription for the controlled substances for the patient.

18. The apparatus of claim 17 wherein the rules engine compares a picture of the controlled substance as it is being dispensed to a picture of the controlled substance listed in the prescription.

19. The apparatus of claim 11 wherein the rules engine compares a location of a patient with a location where the controlled substance is dispensed for said patient.

20. An apparatus for monitoring network packets on a network, the apparatus comprising:
  a network interface means, said network interface means configured to promiscuously invigilate all traffic on the network, where the network interface means filters out all network traffic except application layer packets;
  a database for storage of information from the application layer packets;
  a processor unit connected to the database and the network interface means;
  wherein the processor unit executes an algorithm to parse the application layer packets and filter out packets that relate to controlled substances, sending the application layer packets related to the controlled substances to a rules engine means and a machine learning rules means;
  wherein if the rules engine means or the machine learning rules means determine that the application layer packets relate to the controlled substances, the application layer packets related to the controlled substances is sent for further review.

* * * * *